United States Patent [19]
Griffin

[11] Patent Number: 6,035,905
[45] Date of Patent: *Mar. 14, 2000

[54] FILLING CONTAINERS WITH PARTICULATE MATERIAL

[75] Inventor: David Peter Griffin, Cambridge, United Kingdom

[73] Assignee: Merck Patent Gesellschaft mit beschrankter Haftung, Darmstadt, Germany

[ * ] Notice: This patent is subject to a terminal disclaimer.

[21] Appl. No.: 09/068,645

[22] PCT Filed: Nov. 14, 1996

[86] PCT No.: PCT/GB96/02794

§ 371 Date: Aug. 14, 1998

§ 102(e) Date: Aug. 14, 1998

[87] PCT Pub. No.: WO97/18991

PCT Pub. Date: May 29, 1997

[30] Foreign Application Priority Data

Nov. 17, 1995 [GB] United Kingdom .................. 9523555

[51] Int. Cl.⁷ ..................................................... B67C 3/26
[52] U.S. Cl. ........................... 141/181; 141/67; 141/100; 141/102; 141/103; 141/182; 141/236; 141/237; 141/238; 141/244; 141/250
[58] Field of Search ................................. 141/2, 4, 5, 8, 141/67, 100–103, 181–182, 184, 185, 236–238, 244, 250, 286, 297, 325–327; 53/471, 478, 539

[56] References Cited

U.S. PATENT DOCUMENTS

| 249,544 | 11/1881 | Pritchard | 141/237 |
|---|---|---|---|
| 3,718,164 | 2/1973 | Stewart | 141/1 |
| 4,731,979 | 3/1988 | Yamamoto et al. | 53/529 |
| 4,751,948 | 6/1988 | Hertig et al. | 141/67 |
| 4,884,602 | 12/1989 | Yamamoto et al. | 141/242 |
| 5,775,389 | 7/1998 | Griffin | 141/325 |

FOREIGN PATENT DOCUMENTS

| 93/16748 | 9/1993 | WIPO . |
|---|---|---|
| 95/31239 | 11/1995 | WIPO . |

*Primary Examiner*—Steven O. Douglas
*Assistant Examiner*—Timothy L. Maust
*Attorney, Agent, or Firm*—Millen, White, Zelano & Branigan

[57] ABSTRACT

A multi-compartment container is charged with a plurality of doses of powdered medicament so that the volume of each dose is than that of the respective compartments in which it is contained. A respective protuberance is inserted into each respective compartment, which is then filled with medicament and the protuberance is then removed. The container may take the form of an apertured plate, in which case the filling step can be achieved by placing the container on a porous bed and in communication with a reservoir of particulate material, and then passing gas through the reservoir, the apertures in the container and the bed. There is also shown apparatus for performing the method, the apparatus comprising a reservoir for the particulate material and a conduit for relaying particulate material from the reservoir to the compartments, the conduit including protuberances which are insertable into the compartments to reduce the available volume of the latter. The size of the doses can be controlled by appropriate selection of protuberance dimensions, and a plate-type container, when filled by the method, can be relatively easily sealed by, for example, the application of laminated foil.

14 Claims, 12 Drawing Sheets

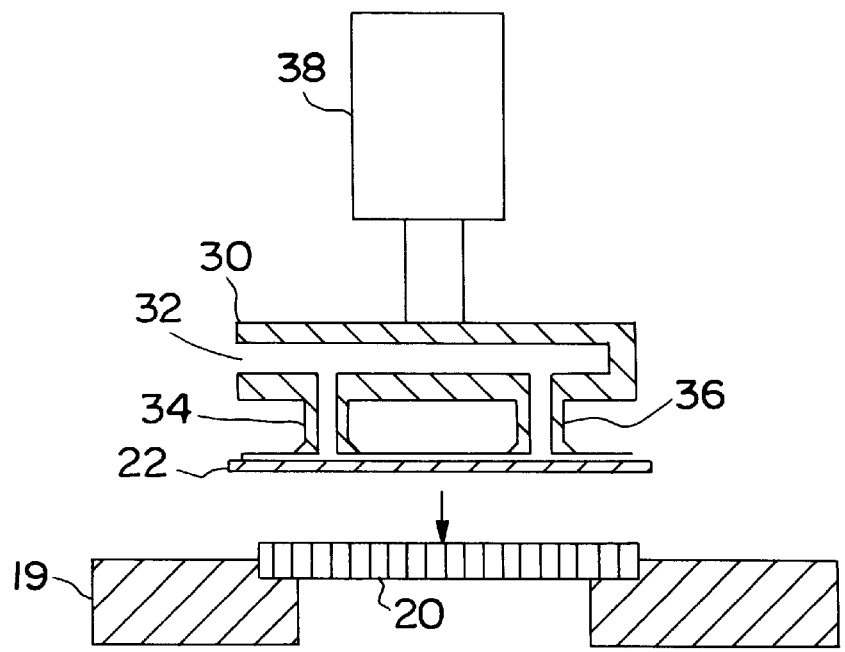
F I G. 2
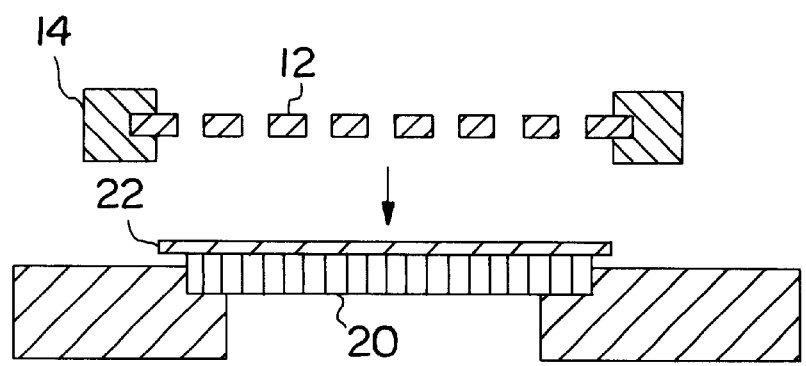
F I G. 3
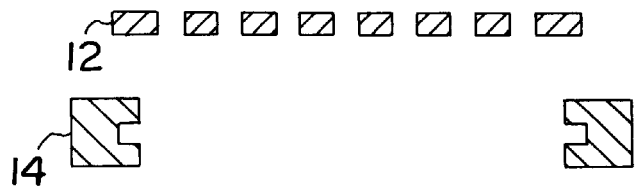
F I G. 4

FILLING CONTAINERS WITH PARTICULATE MATERIAL

FIELD OF THE INVENTION

This invention relates to a method of and apparatus for introducing each of a plurality of doses of particulate material into a respective compartment of a container. The invention is particularly applicable to the loading of a multi-compartment container with a powdered medicament.

BACKGROUND OF THE INVENTION

Co-pending PCT Patent Application No PCT/GB94/02716 (Publication No WO95/16483) describes a method of filling a container such as may be used in an inhaler for dispensing medication for respiratory complaints. In that method, the container, which takes the form of a flexible plate, is laid flat on a porous bed and an excess of powdered medicament applied to one face of the plate. Gas pressure is then used to urge the medicament into apertures in the plate, which is then wiped clean of any excess of powdered medicament and sealed on opposite faces with laminate foil so that each aperture of the plate holds a respective individually encapsulated dose of medicament.

In this method, the volume of each dose is determined by the capacity of each aperture in the plate, and cannot therefore be altered for any given container. In addition, residual traces of particulate material must be removed from the face of the plate before the foil laminate is applied, otherwise the effectiveness of the seal between the foil and the plate may be compromised.

SUMMARY OF THE INVENTION

According to the first aspect of the invention, there is provided a method of introducing each of a plurality of doses of particulate material into a respective compartment of a container, the method comprising the steps of:

a) inserting a respective protuberance into each compartment so as to reduce the capacity thereof;

b) filling each compartment with said particulate material, with the respective protuberance inserted in said compartment; and c) removing said protuberances, wherein the volume of each dose of material is less than that of its respective compartment.

Thus the method enables a container, the compartments of which hitherto would have been completely filled, to hold smaller doses of particulate material. This is a particular advantage if the container is for use as an inhaler since containers of the same basic dimensions can then be used to hold doses of medicament which differ in volume.

In addition, if each compartment is completely filled, with a protuberance inserted, the volume of the resultant dose of material will be the net of the total volume of the compartment and the volume occupied by the protuberance thus, for a given size of compartment, the volume of the dose can be controlled by selecting a protuberance of suitable dimensions.

Preferably, each protuberance comprises a conduit which is inserted part-way into the respective compartment and through which said particulate material is introduced into said compartment.

Preferably, the distance by which each conduit can be inserted into its respective compartment is determined by stop means which engage with the portions of the container around the entrance to the compartment to prevent further insertion.

Conveniently, the container may comprise a plate having a plurality of apertures, each of which constitutes a respective compartment, and in this case the apertures are preferably filled by the steps of positioning the plate on a porous bed with the apertures in communication with a reservoir of particulate material; applying gaseous pressure to the material in the reservoir so as to transfer particulate material from the reservoir to the apertures, the porosity of the bed being such as to allow the passage of gas but to prevent the particulate material from passing all the way through the apertures and escaping from the underside of the plate. Preferably, the gas is passed through the porous bed via the reservoir and the apertures.

The use of gas provides additional control over the force with which the particulate material is urged into the apertures, and hence the density of the material therein.

Preferably, the bed comprises a perforated base plate and a sheet of finely porous material, for example filter paper, interposed, in use, between the base plate and the container.

The apertures, once filled, are preferably sealed so that each dose is individually encapsulated in its respective aperture, and said sealing is conveniently achieved by bonding a respective sheet of material to each face of the plate.

Preferably, this is achieved by bonding a sheet of material to the uppermost face of the plate while the plate is supported on a support for preventing material escaping from the apertures, inverting the plate, and the support, removing the support to expose the opposite face of the plate, which is then the uppermost face and bonding a sheet of material to said opposite face.

Preferably, the support comprises the porous bed.

Since the volume of each dose is less than that of its respective compartment, it tends not to stand proud of the upper face of the plate so that the upper face can be kept relatively clear of particulate material, thus facilitating bonding of the sheet material. The same advantage applies to the sealing of the opposite face since the subsequent inversion of the plate will allow material to move away from that lower face.

Preferably, the sheet material which seals the apertures comprises a laminated foil which is attached to the body by being heat sealed thereto.

The laminated foil tends to resist any tendency for fragments of the sheet to be broken away from the rest of the sheet when the seal for a given compartment is ruptured to allow material to be discharged from that compartment.

The plate may be flexible, in which case the method preferably includes the steps of rolling or otherwise forming the plate into a cylinder once it has been filled.

The container may be retained in its cylindrical configuration by applying an annular end cap thereto, typically two said end caps are used one at each end.

The plate preferably comprises an array of elongated flat, substantially rigid strips, adjacent pairs of which are hingeable relative to each other, such that the strips are substantially parallel to the axis of the cylinder in the finished container.

Alternatively, the plate can constitute one of a number of strips which are fitted together to form a cylindrical composite container.

Preferably, the particulate material is a powdered medicament.

According to a second aspect of the invention, there is provided apparatus for introducing a respective dose of particulate material into each of a plurality of compartments of the container, the apparatus comprising a reservoir for said particulate material, conduit means for conveying particulate material from the reservoir to the compartments when the latter are in registry with the conduit means, and a plurality of protuberances, each being insertable into a respective compartment temporarily to reduce the capacity of the compartment, so that the volume of each dose is less than that of the compartment in which it is contained.

Preferably, the protuberances form part of the conduit means, and comprise a plurality of conduits, each of which is insertable part of the way into a respective compartment.

Preferably, the apparatus is arranged to fill a container which comprises a plate, in which case, the conduits preferably project from a filling plate which, in use, engages the container to limit the distance by which the conduits can be inserted into compartments.

BRIEF DESCRIPTION OF THE DRAWINGS

A method and apparatus in accordance with the invention will now be described, by way of example only, with reference to the accompanying drawings in which:

FIG. 2 is a diagrammatic sectional view, taken in a radial plane and to an enlarged scale, illustrating the activity carried out at the first of said stations;

FIG. 3 is a diagrammatic sectional view, taken in a radial plane and to an enlarged scale, illustrating the activity carried out at the second of said stations;

FIG. 4 is an exploded sectional side view of two of the components shown in FIG. 3;

DETAILED DESCRIPTION

The apparatus shown in the figures is operable to introduce powdered medicament into the compartments of a container similar to that shown in FIGS. 15A to 15E of published PCT specification No WO95/16483. The apparatus also seals the container and rolls it into a cylinder for use with a dispenser of (or similar to) the kind shown in FIGS. 3 to 11 of WO95/16483.

The container comprises a plate formed from an array of parallel plastic strips, each of which is hingely connected to its neighbouring strips and includes a line of apertures. When the container is rolled into its cylindrical form, all the apertures lie on a helical path.

The number of strips, and the number of apertures in each strip, depends on the number of doses of medicament to be contained in the container. The container shown in the figures has a total of fourteen apertures arranged in seven strips, each of which has two apertures. However, the apparatus could be modified so as to be capable of filling containers having different numbers of apertures.

Figure 1:
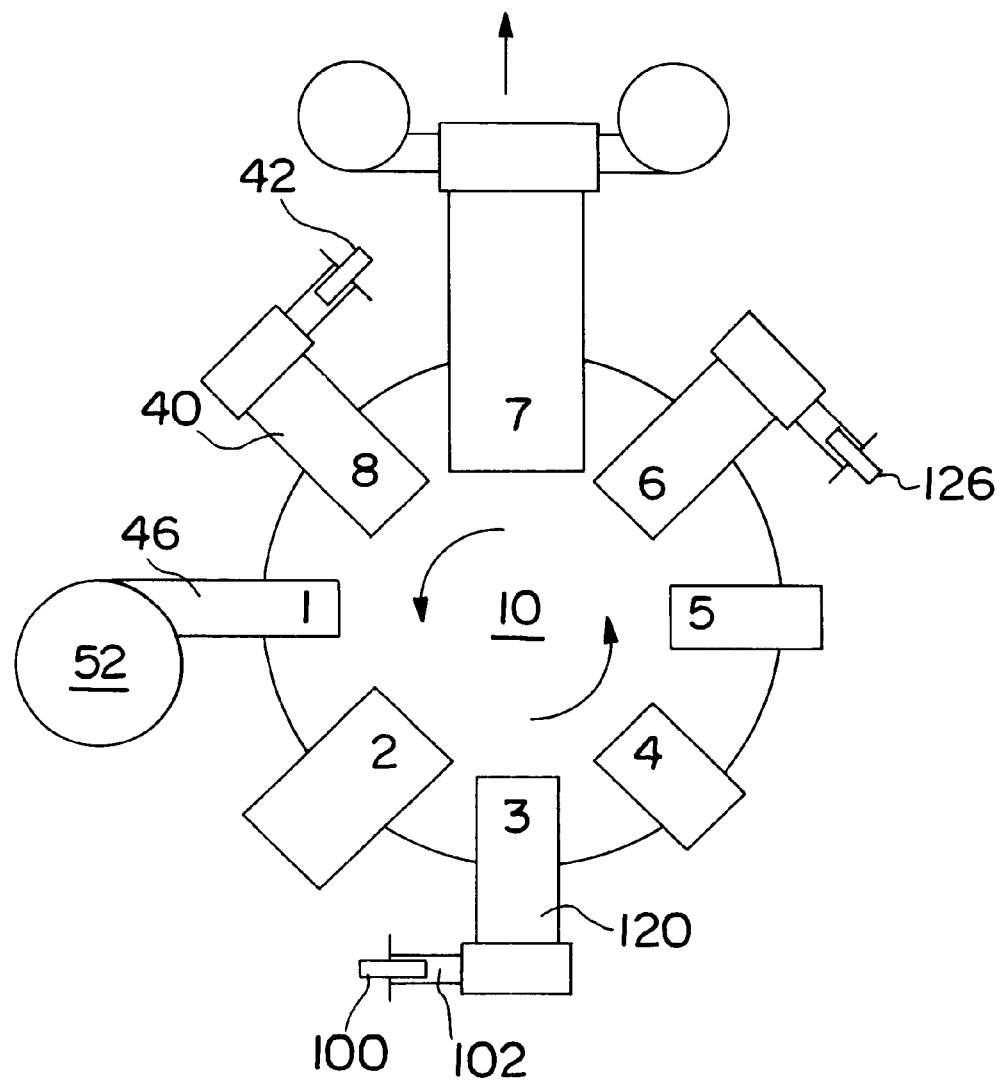
FIG. 1 is a plan view of the apparatus which has eight stations, arranged around a carousel, at which various operations are performed.
Figure 5:
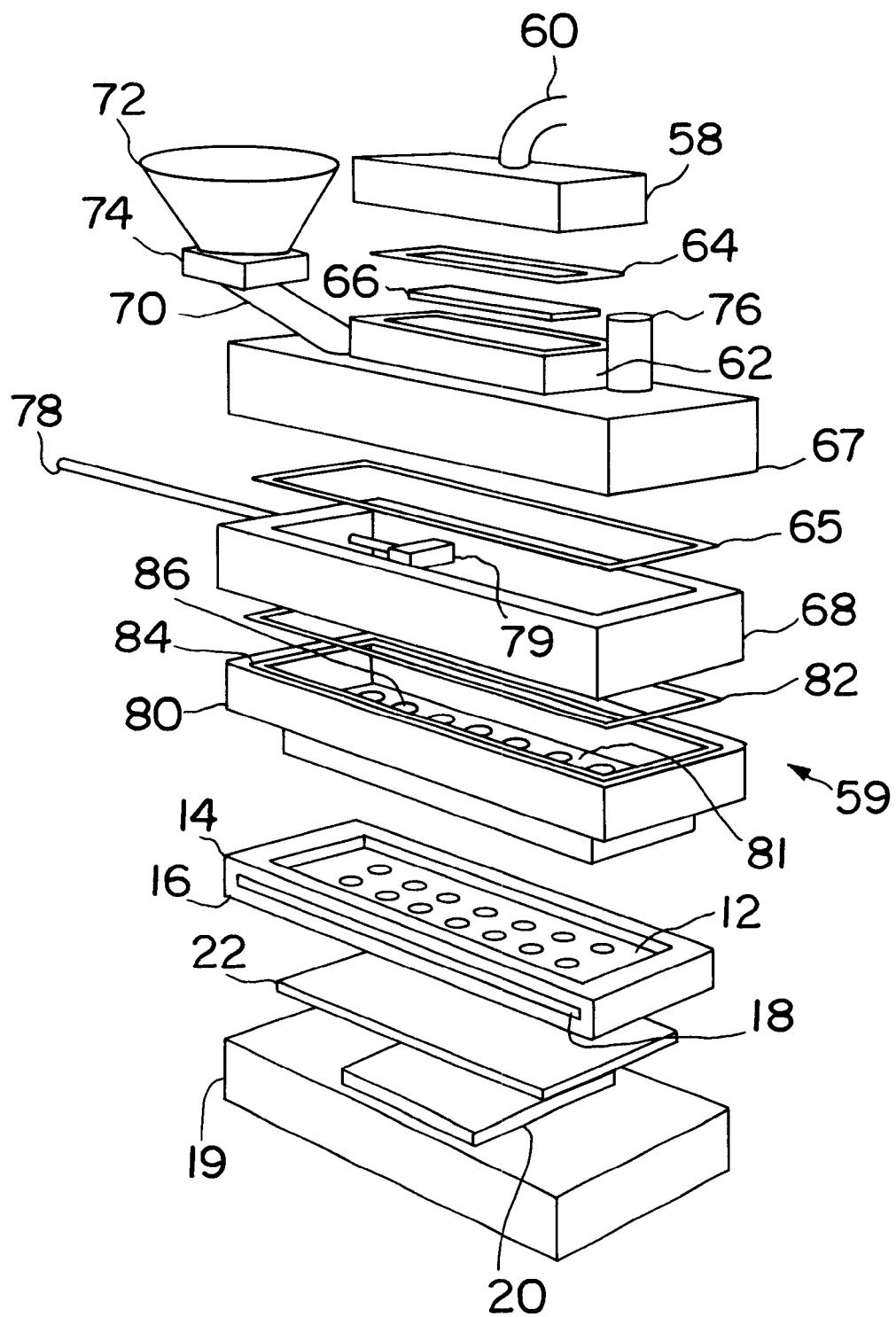
FIG. 5 is an exploded isometric view of a filling station, which is the third station of the device, the Figure also showing the components transferred from the second station to the filling station.
Figure 6:
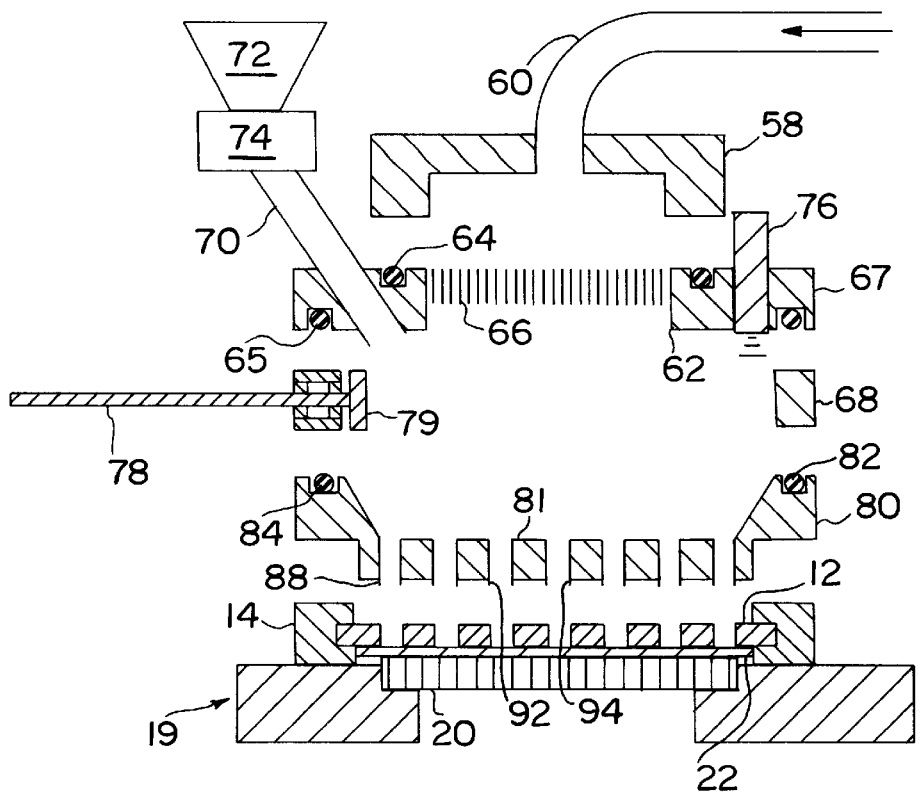
FIG. 6 is an exploded radial sectional view of the filling station.

With reference to FIG. 1, the apparatus comprises a carousel 10 and eight stations 1 to 8 positioned around the periphery thereof. In use, the carousel rotates in an anticlockwise direction to transport components on the carousel to each of the stations in turn, as described below.

FIG. 4 shows a container 12 to be filled and sealed by the apparatus. During the filling sealing of the container 12, it is held within a holder 14, which is shown in more detail in FIG. 5. The holder 14 comprises a rectangular frame which is so shaped as to extend around the periphery of the container 12, and which carries a channel which runs along the inner periphery of three of the four sides of the frame 14. The fourth side, referenced 16, incorporates an aperture 18 through which the container 12 can be inserted into or removed from the frame 14.

When the container 12 is inserted into the frame 14, its edges are held within the channel, so as to locate and retain the container 12 in the frame 14.

With reference to FIG. 2, the frame 14 and the container 12 are carried on the carousel 10 through the stations 2–4 on a support block 19 which carries a perforated metal block 20.

However, before the frame 14 and container are placed on the support 19, the station 8 applies a piece of filter paper 22 to the block 20 as shown in FIG. 2.

To that end, the station 8 includes a head 30 which has a central passage 32 which communicates with two feet 34 and 36. The passage 32 is selectably connected to a source of vacuum (not shown), and the head 30 is mounted on a pneumatic piston and cylinder assembly 38 which is operable to raise and lower the head 30. The piston and cylinder assembly 38 is, in turn, suspended from an upper plate 40 (FIG. 1) through drive means (not shown) operable to move the assembly 38, and hence the head 30 radially relative to the carousel 10.

A reel 42 of filter paper is provided at the radial outer end of the station 8, which includes a punch and die mechanism (not shown) for cutting the filter paper to length.

The head 30. in use, retrieves a cut-out piece of filter paper from the radial outer end of the station 8, a vacuum being applied to the passage in the head to retain the cut-out 22 on the feet, conveys it radially inwards to the position shown in FIG. 2, and then lowers the filter paper 22 onto the block 20. The vacuum is then disconnected so that when the head is raised, the filter paper remains on the block 20.

The support is then conveyed on the carousel 10 to the station 1. The station 1 has a pneumatic gripper which is mounted on an upper plate 46 through a pneumatic piston and cylinder assembly, which is moveable along the plate 46.

In use, the gripper collects a container, such as the container 14 which has been pre-loaded into a frame such as frame 14, from a magazine 52 at the radial outer end of the station 1, conveys the container and frame to the position shown in FIG. 3 and places them on the support 19 so that the filter paper 22 is in registry with the container 12. The gripper is then removed.

The support 19, with the container 12, frame 14 and filter paper 22 thereon is then transported to the filling station 2 which is shown in FIGS. 5 to 11.

The filling station 2 comprises a filling head assembly 59 having a rectangular inlet manifold 58 which communicates with a pipe 60 through which pressurised nitrogen can be selectively supplied to the manifold. The manifold 58 is sealed against a rectangular upper frame portion 62 by an o-ring seal 64 seated in a rectangular groove extending around the top of the portion 62. The portion 62 includes a central rectangular opening which accommodates a diffuser 66 in the form of a perforated block, a peripheral rectangular frame portion 67 surrounds the portion 62, and defines, with the portion 62, an inlet aperture which accommodates an inlet chute 70, along which powdered medicament is supplied, in use, from an auger 72 via valve 74. The frame portion 67 also has an aperture opposite said chute 70 for accommodating an ultrasonic level sensor 76. The outer frame portion 67 is sealed against a lower rectangular frame portion 68 by means of an o-ring seal 65 seated in a rectangular peripheral groove extending around the bottom of the portion 67. The frame portion 68 includes an aperture in one side thereof through which a rod 78 extends. The end of the rod is attached to a rectangular plate 79, the elongate axis of which extends substantially perpendicularly to the plane of FIGS. 6 to 11.

A hopper 80 is sealed against the base of the frame portion 68 by an o-ring seal 82 seated in a rectangular groove 84 in the top of the hopper 80. The bottom of the hopper 80 comprises a plate 81, which includes a skewed rectangular array of fourteen holes, one of which is denoted 86, in positions corresponding to the positions of the apertures in the container 12.

The lower surface of the plate 81 is formed with an array of downwardly projecting cylindrical nozzles, for example 88, 92 and 94 (FIGS. 6 to 11), each of which is in registry and communicates with a respective aperture in the plate 81.

Figure 7:
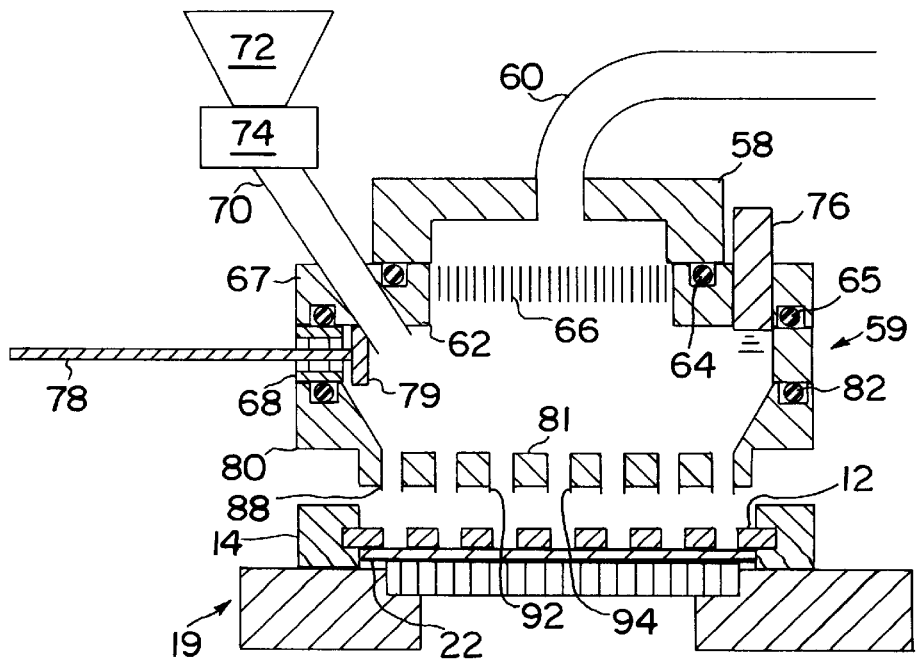
FIGS. 7 to 11 are radial sectional views of the filling station at various stages of its operation.
Figure 8:
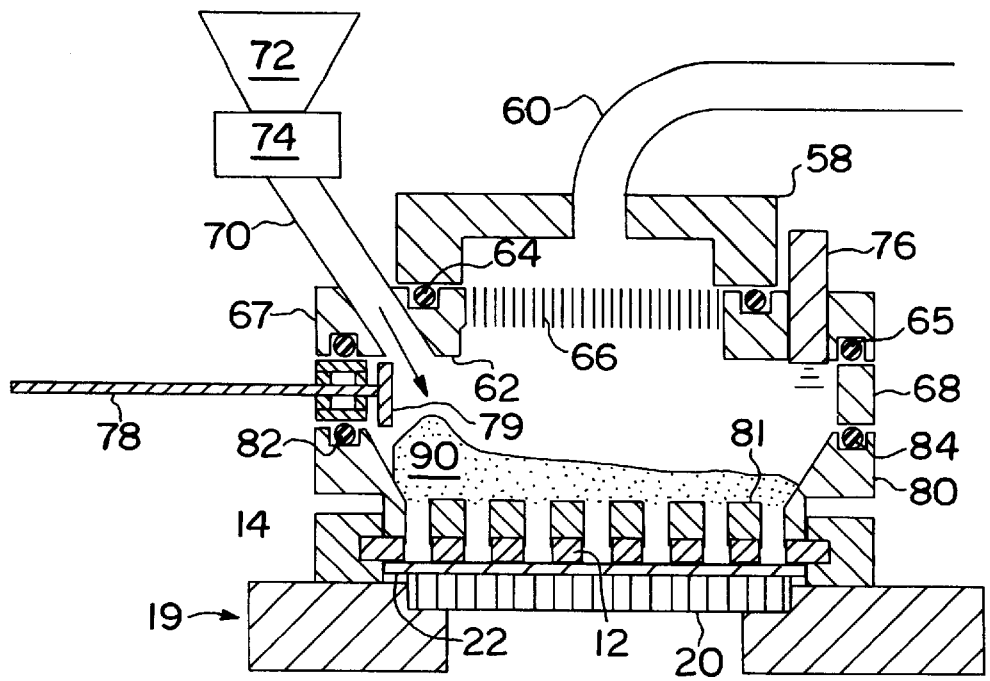

The filling head 59 and container 12 can be lowered from the position shown in FIG. 7 to that shown in FIG. 8, in which the plate 81 closely abuts the container 12, the holes in the plate 81 register with the apertures in the container 12, and the nozzles in the plate 81 extend part way into the apertures in the container 12.

Figure 9:
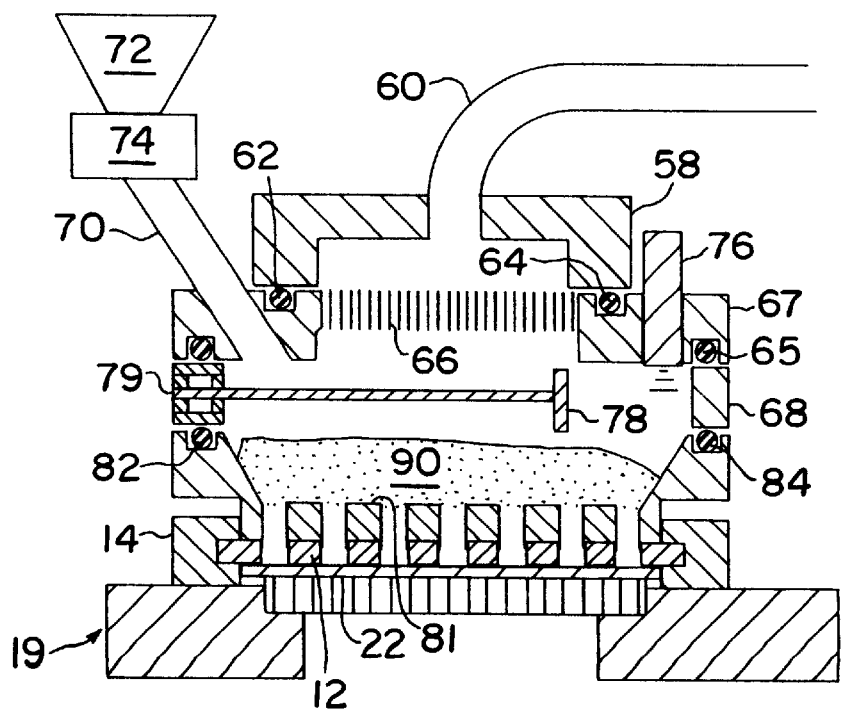

Powdered medicament 90 can be introduced into the hopper through the chute 70. The detector 76 is operable to sense the level of the medicament 90 at the end of the hopper opposite the chute 70, and if that level is insufficient, the rod 78 is extended, causing the plate 79 to redistribute the medicament 90 over the holes in the plate 81, as shown in FIG. 9.

Figure 10:
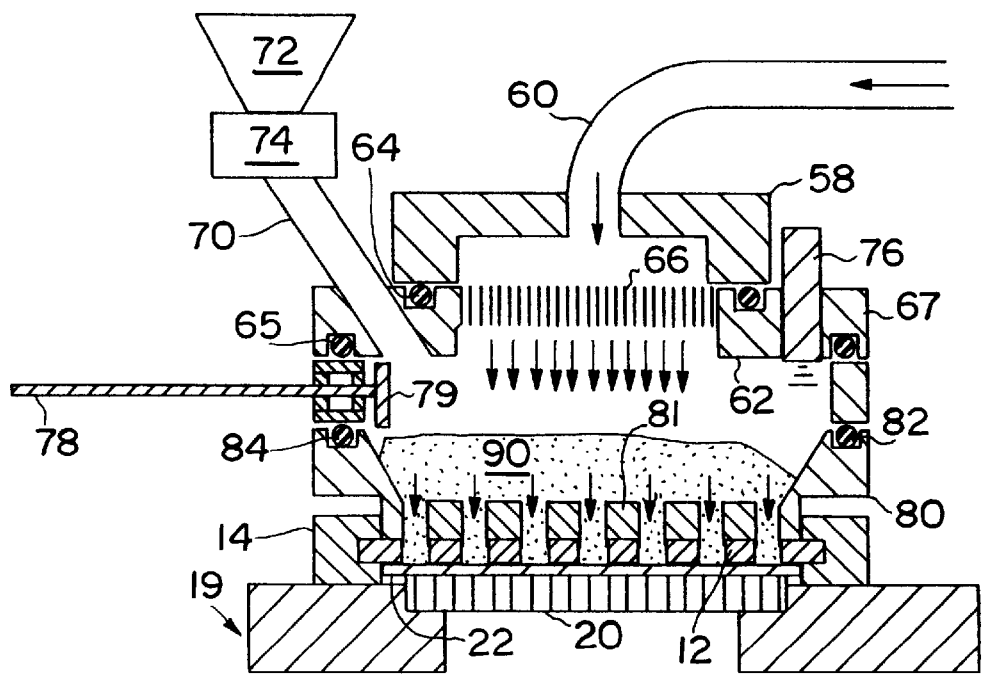

The container 12 is filled, by introducing nitrogen under pressure through the pipe 60. The nitrogen passes through the diffuser 66 (which prevents the flow of nitrogen adversely affecting the distribution of the particulate material 90) through the material 90, the holes and nozzles in the plate 81 and through the apertures in the container 12 (FIG. 10). Nitrogen exiting the apertures in the container 12 passes through the block 20 via the filter paper 22. This passage of nitrogen urges the powdered medicament 90 through the holes and nozzles in the plate 81 and into the apertures in the container 12, whilst the filter paper 22 prevents the powdered medicament being expelled through the bottom of the apertures of the container 12.

Figure 12:
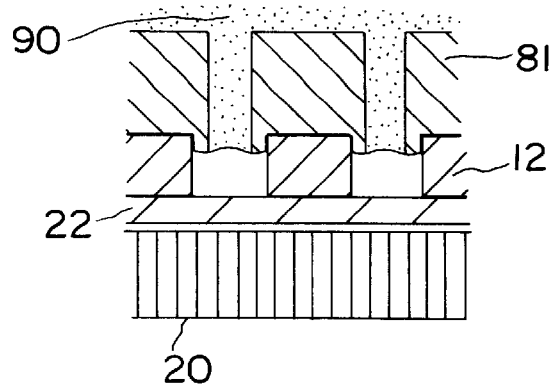
FIGS. 12 to 14 are fragmentary close up sectional views of part of the filling station and a container, and show the sequence of steps involved in filling the container.
Figure 13:
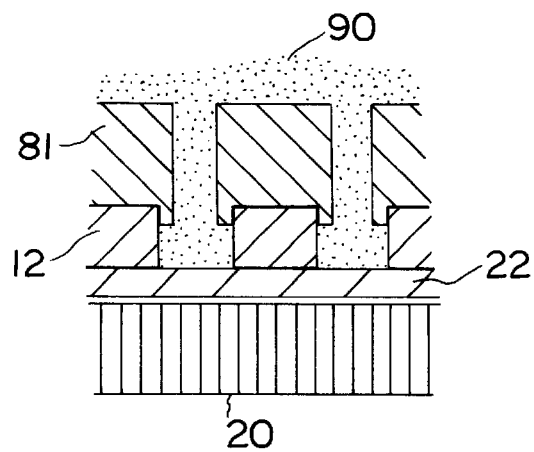
Figure 14:
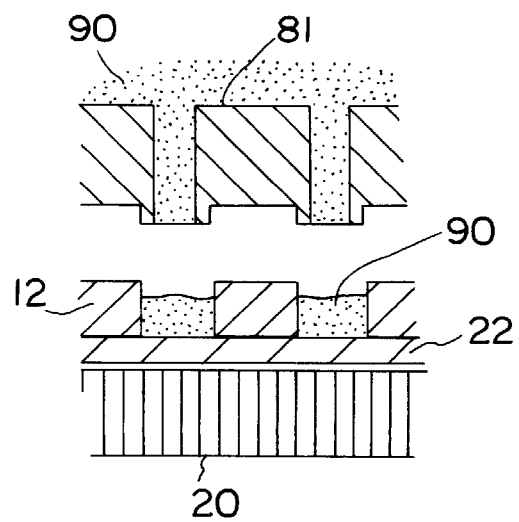

Three stages during the movement of medicament from the hopper 80 to the container 12 are illustrated in FIGS. 12 to 14. Medicament passes into each aperture in the container 12 so that all the available volume of the aperture, i.e. the total volume of the aperture minus the volume of the nozzle therein, is occupied by the powder, as shown in FIG. 13.

The supply of nitrogen is then interrupted, and the hopper 80, and the filling head 59 is then raised. When the hopper 80 is not pressurised with nitrogen, the powdered medicament in the nozzles forms "bridges" thereacross so that, on raising the filling head 59, the level of powder left in the apertures in the container 12 is substantially the same as the level of the bottom of the nozzles, when inserted in the apertures (FIG. 14).

Thus the nozzles allow the apertures in the container 50 to contain doses of medicament which are of a lower volume than that of the apertures. The volume of dose can also be readily adjusted by replacing the plate 81 with another plate having nozzles of a different height, or applying packing to the underside of the plate 81 so that the nozzles cannot project so far into the apertures in a container. In addition, the plate 81 can be replaced by another having nozzles, some of which are higher than the others so as to project further into the container 12 than the others. In such an arrangement, some apertures in the plate 12 would be provided with larger doses than others.

Figure 11:
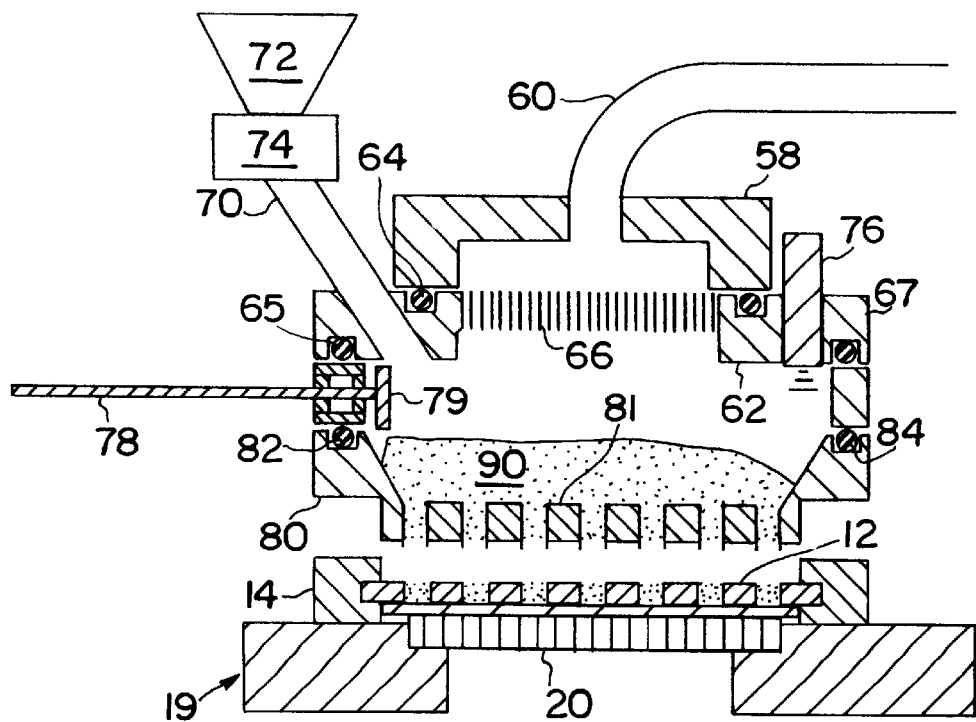
Figure 15:
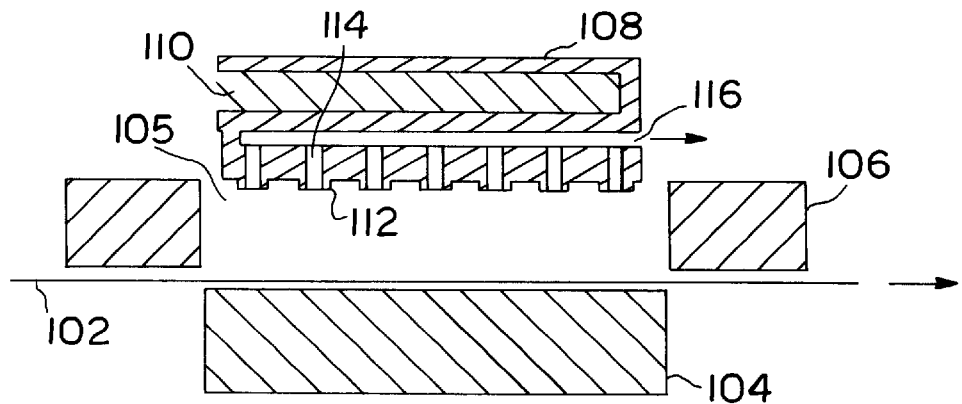
FIGS. 15 to 19 are radial sections of parts of the fourth station at various stages in one cycle of operation.

Once the filling head 59 has been raised from the container 12, as shown in FIG. 11, a further charge of powdered medicament is poured into the hopper for the next filling, and if necessary the powder is levelled by the plate 79. The filled container 12 and its holder 14 are then transported by the carousel 10 to the station 3 which includes, at its radial outer end, a reel 100 of a web 102 of foil laminate (FIGS. 15–17), and feed-means (not shown) for feeding foil from the reel past a punch 104 and a die 106, which die defines a rectangular aperture 105 (FIG. 15). A sealing head 108 is positionable so that it is in registry with the aperture defined by the die 106, and is connected to a pneumatic piston and cylinder assembly (not shown) which is operable to raise and lower the head 108.

The head 108 includes a heater 110 and a number of feet, one of which is referenced 112, arranged in a skewed rectangular array on the underside of the head 108. Each foot is in the form of a short hollow cylinder, the interior of which communicates with a respective vertical passage, for example 114. The vertical passages, in turn, communicate with a horizontal common passage 116 which is selectively connectable to a vacuum source (not shown).

Figure 16:
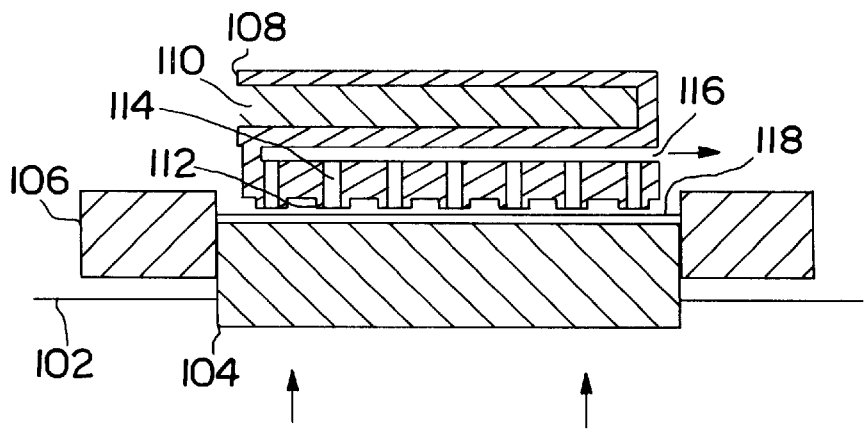
Figure 17:
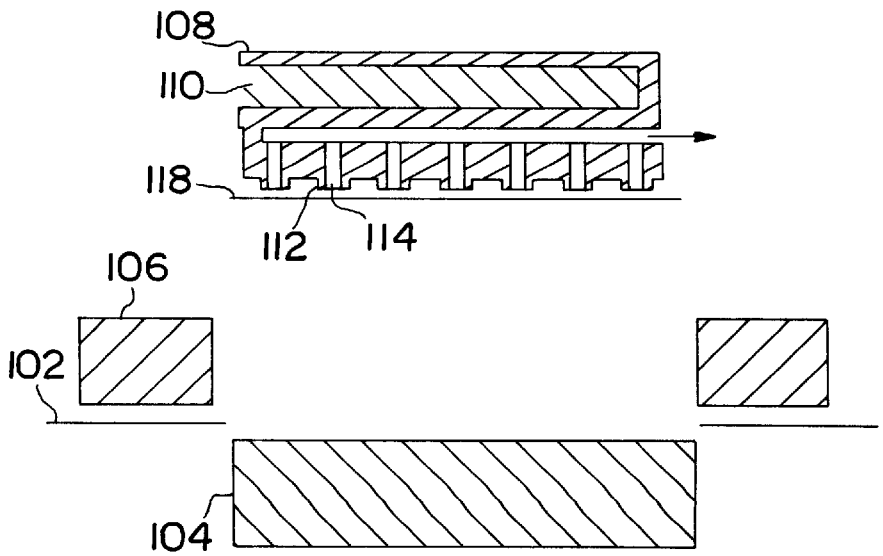

With reference to FIG. 16, the punch 104 is also mounted on a pneumatic piston cylinder arrangement (not shown) which is operable to raise the punch 104, causing it to cut from the length of foil 102 a rectangular piece 118 which is moved up into contact with the head 108. As this happens, the passage 116 is connected to the vacuum source which causes the feet on the head 108 to hold the piece 118 thereon.

The web of foil 102 is wider than the cut-out 118, and as a result, when the punch 104 is returned to the position shown in FIG. 15, a fresh piece of foil can he drawn into position above the punch 104 by means of a reel assembly (not shown) positioned to the right of the components shown in FIGS. 15 and 16, which is on the opposite side of those components from the reel 100.

Figure 18:
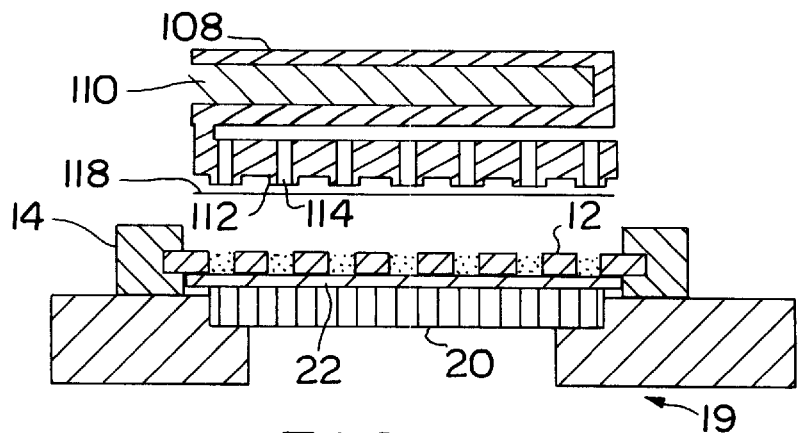

The piston and cylinder attached to the head 108 is mounted on a top plate 120 (FIG. 1) via a drive mechanism for moving the head 108 in either radial direction. Thus, once the cut-out 118 has been attached to the head 108, the latter is raised into the position shown in FIG. 17 and the drive means operates to move the head radially inwards into the position shown in FIG. 18, in which it is positioned above the container 12, which has been moved on the carousel 10 to the radial inner portion of the station 3.

Figure 19:
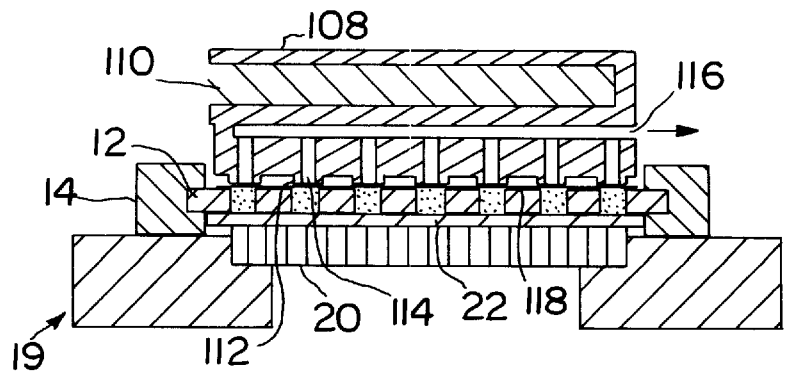

The head 108 is then lowered onto the container 12 as shown in FIG. 19. The foil laminate of the cut-out 118 has an upper layer (in contact with the feet on the head 108) which is substantially unaffected by the heat from the heater 110. However, the lowermost layer of the laminate is partially fused by the heat from the heater 108, causing the cut-out 118 to be heat-sealed to the container 12. The passage 116 is then disconnected from the vacuum supply, and the head 108 is raised and returned to the position shown in FIG. 15, leaving the container 12 with a foil laminate seal on one face.

Figure 20:
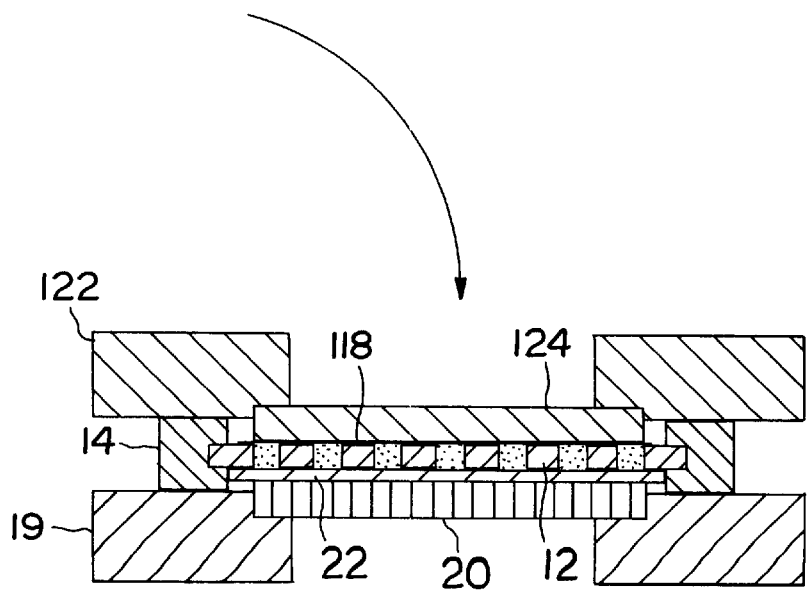
FIGS. 20 and 21 are similar views illustrating the operations carried out at the fifth station.
Figure 21:
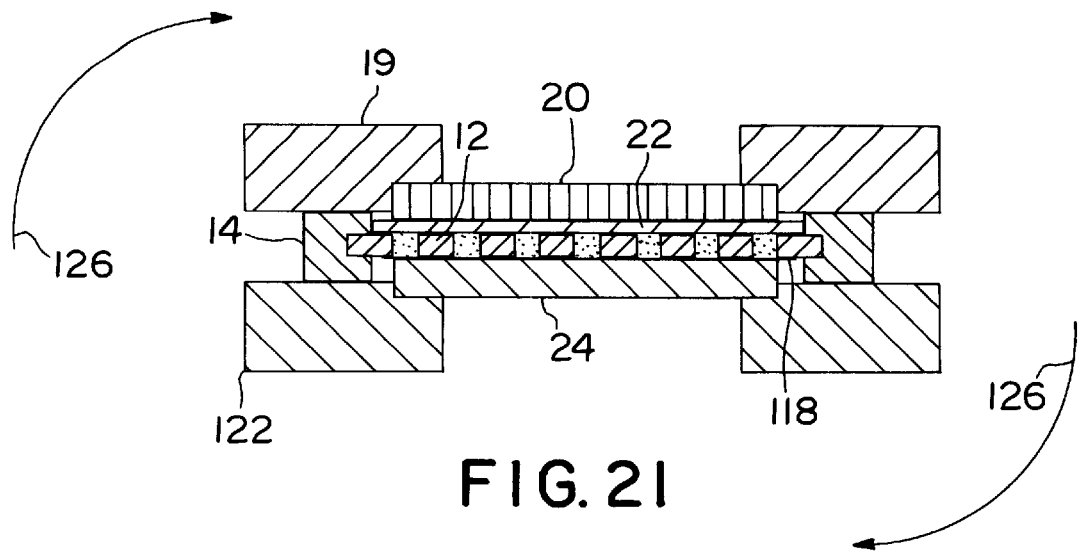

With reference to FIG. 20, the container 12 and its support 19 are then transported to the station 4 at which the container 12, the support 19 and the block 20 are removed from the carousel 10 and support block 122 similar to the block 19, and a solid plate 124, are then placed on top of the container 12 and frame 14. The support blocks 19 and 122 are connected to a mechanism (not shown) which inverts the elements shown in FIG. 12 in the way indicated by the arrows 126 in FIG. 21 so that the support block 19 and perforated block 20 are then uppermost. The components shown in FIG. 21 are then transported to the station 5 which includes a head (not shown) which releasably grips the top of the support block 19 and which has a suction mechanism which seals against the block 20, to cause the filter paper 22 to be held against the block 20. The head is then moved away from the container 12, taking the blocks 19 and 20 and the paper 22 with it, as shown in FIG. 22.

Figure 22:
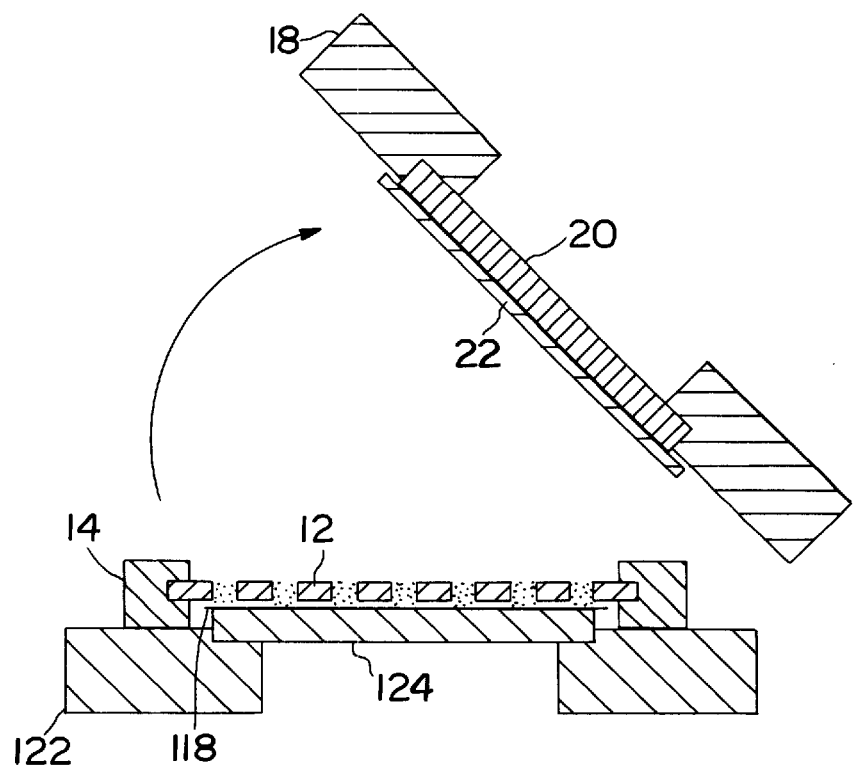
FIG. 22 is a similar view of the sixth station.

The remaining elements shown in FIG. 22 are then transported to the station 6 which is similar in form and function to the station 8, and which thus includes a reel 126 of foil laminate which is fed to a punch and die assembly similar to the punch 104 and die 106.

Figure 23:
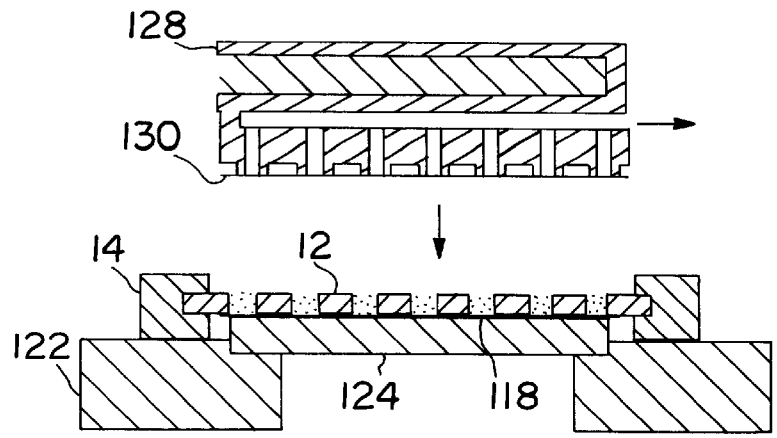
FIG. 23 shows parts of the seventh station.

The punch and die cut out a piece of the foil laminate 130 (FIG. 21), which is then applied to a head 128 of the same kind as the head 108. The head 128 is mounted at the station 8 by a similar arrangement used to mount the head 108 on the station 3, so that the head 128 can move radially into the position shown in FIG. 23 in which it is directly above the container 12. The head is then lowered, sealing the cut-out piece of foil laminate 130 to the container 12.

Figure 24:
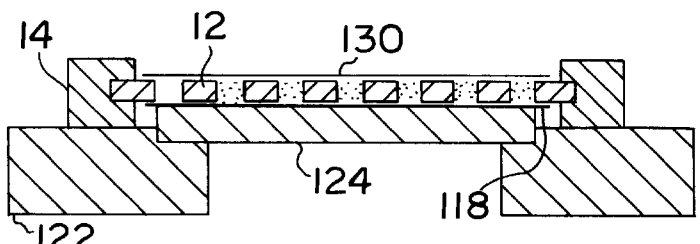
FIG. 24 shows, in radial section, the elements which are transported from the seventh station to the eighth station.

FIG. 24 shows the container 12 in its filled and sealed form, still in its frame 14. In this form, the container 12 and frame 14 are fed to the station 7 at which the container 12 is removed from the holder 14 and rolled into the form of a cylinder in a similar fashion to the method previously described in WO 95/16483.

Figure 25:
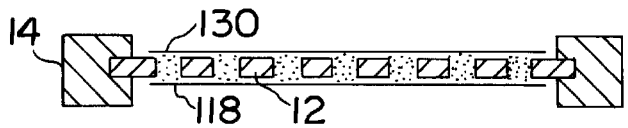
FIGS. 25 and 26 illustrate two of the operations carried out at the eighth station.
Figure 26:
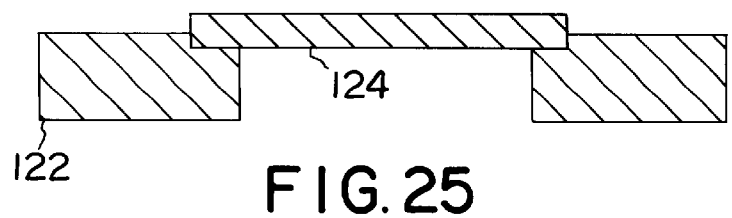
Figure 26:
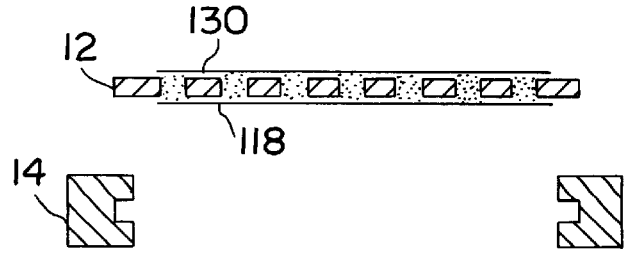
Figure 27:
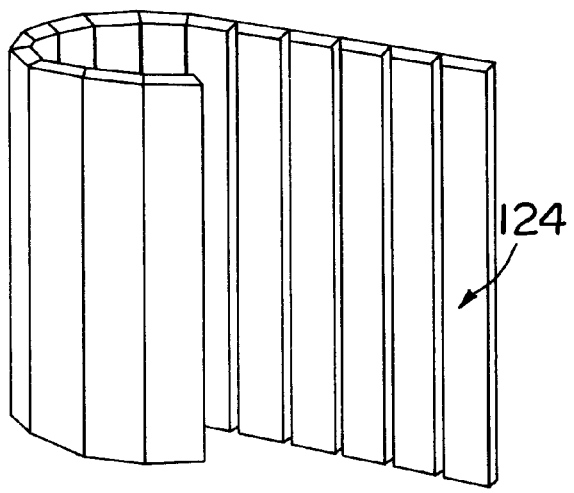
FIG. 27 illustrates a plate being rolled into a cylinder.
Figure 28:
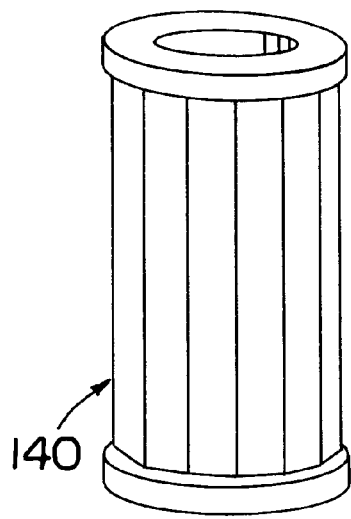

FIG. 25 shows the container 12 and frame 14 after they have been separated (in the station 7) from the block 122 and plate 124, and FIG. 26 shows the (filled and sealed) container after having been removed from the frame 14. FIGS. 27 and 28 show the plate 124 being formed into a cylinder 140.

I claim:

1. A method of introducing each of a plurality of doses of particulate material into a respective compartment of a container, the container comprising a plate having a plurality of apertures, each of which constitutes a respective compartment, the method comprising the steps of:

a) inserting a respective protuberance into each compartment so as to reduce the capacity thereof;

b) filling each compartment with said particulate material, with the respective protuberance inserted in said compartment by positioning the plate on a porous bed with the apertures in communication with a reservoir of particulate material; applying gaseous pressure to the reservoir so as to transfer particulate material from the reservoir to the apertures, the porosity of the bed being such as to allow the passage of gas but to prevent the particulate material from passing all the way through the apertures and escaping from the underside of the plate; and c) removing said protuberances, wherein the volume of each dose of material is less than that of its respective compartment.

2. A method according to claim 1, in which each protuberance comprises a conduit which is inserted part-way into the respective compartment and through which said particulate material is introduced into said compartment.

3. A method according to claim 2, in which the distance by which each conduit can be inserted into its respective compartment is determined by stop means which engage with the portions of the container around the entrance to the compartment to prevent further insertion.

4. A method according to claim 1, in which the application of gaseous pressure involves passing a gas through the reservoir, the apertures and the porous bed.

5. A method according to claim 4, in which the bed comprises a perforated base plate and a sheet of finely porous material, for example filter paper, interposed, in use, between the base plate and the container.

6. A method according to claim 5, in which the apertures, once filled, are sealed so that each dose is individually encapsulated in its respective aperture.

7. A method according to claim 6, in which said sealing is achieved by bonding a respective sheet of material to each face of the plate.

8. A method according to claim 7, in which the container is sealed by bonding a sheet of material to the uppermost face of the plate while the plate is supported on a support for preventing material escaping from the apertures, inverting the plate, and the support, removing the support to expose the opposite face of the plate, which is then the uppermost face and bonding a sheet of material to said opposite face.

9. A method according to claim 8, in which the support comprises the porous bed.

10. A method according to claim 8, in which the sheet material which seals the apertures comprises a laminated foil which is attached to the body by being heat sealed thereto.

11. A method according to claim 10, in which the plate is flexible, and the method includes the steps of rolling or otherwise forming the plate into a cylinder once it has been filled.

12. A method according to claim 11, in which the container is retained in its cylindrical configuration by applying an annular end cap thereto.

13. A method according to claim 11, in which the plate comprises an array of elongated flat, substantially rigid strips, adjacent pairs of which are hingeable relative to each other, such that the strips are substantially parallel to the axis of the cylinder in the finished container.

14. A method according to claims 1, in which the particulate material comprises a powdered medicament.

* * * * *